(12) United States Patent
Liu (10) Patent No.: US 6,440,283 B1
(45) Date of Patent: Aug. 27, 2002

(54) OXYGEN SENSOR AND EMISSION CONTROL SYSTEM

(75) Inventor: Meilin Liu, Norcross, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 09/453,283

(22) Filed: Dec. 2, 1999

Related U.S. Application Data (60) Provisional application No. 60/110,628, filed on Dec. 2, 1998.

(51) Int. Cl.[7] ............................................. G01N 27/26
(52) U.S. Cl. ...................... 204/429; 204/425; 204/426
(58) Field of Search ................................ 204/421–429

(56) References Cited

U.S. PATENT DOCUMENTS

| | | | |
|---|---|---|---|
| 3,645,875 A | * | 2/1972 | Record et al. |
| 3,935,089 A | * | 1/1976 | Togawa et al. |
| 4,172,247 A | * | 10/1979 | Ikeura |
| 4,177,112 A | * | 12/1979 | Suzuki et al. |
| 5,695,624 A | * | 12/1997 | Garzon et al. |
| 5,954,930 A | * | 9/1999 | Nafe et al. |
| 6,074,540 A | * | 6/2000 | Kroll et al. |

* cited by examiner

*Primary Examiner*—T. Tung
(74) *Attorney, Agent, or Firm*—Thomas, Kayden, Horstemeyer & Risley, LLP

(57) ABSTRACT

An emission control system for determining a concentration of oxygen in a flow of gas which has a sensor. The sensor has a diffusion barrier, an electrolyte material, and a counter-electrode. The counter-electrode is configured to support the diffusion barrier, and the electrolyte material is disposed between the diffusion barrier and the counter-electrode.

11 Claims, 9 Drawing Sheets

Gas 222

(PRIOR ART)

OXYGEN SENSOR AND EMISSION CONTROL SYSTEM

This application is based on and claims priority to U.S. provisional application, Ser. No. 60/110,628, filed Dec. 2, 1998, which is herein incorporated by reference in its entirety.

TECHNICAL FIELD

The present invention is generally related to oxygen sensors, and, more particularly, systems and methods for measuring the concentration of oxygen in a flow of gas.

BACKGROUND OF THE INVENTION

With continuous improvements and stringency in environmental regulations and advances in emission control technology, there is an intense demand for low-cost, high-sensitivity gas sensors for better control of combustion in order to minimize pollutant emission while improving energy efficiency. One of the most important gas sensors is the solid-state oxygen sensor for control of the air-to-fuel ratio in automobiles, furnaces, and other combustion processes. While potentiometric oxygen sensors have been widely used for control of stoichiometric combustion, they are not adequately sensitive to changes in oxygen concentration when the partial pressure of oxygen in a sample gas is too close to that of a reference gas, typically air, because of the logarithmic response. On the other hand, an amperometric, or a limiting-current type, oxygen sensor exhibits a linear dependence on oxygen concentration in the sample gas. Amperometric sensors are, therefore, more suitable for control of clean-burn combustion.

For a traditional amperometric oxygen sensor, a porous ceramic layer, or a cap with a laser-drilled hole, is used as a diffusion barrier to control the inflow of oxygen. The characteristics of such a sensor depend critically on the micro structure of the diffusion barrier, or the size of the hole. The disadvantages associated with this design include: (i) the pore or hole dimension is difficult to control; and (ii) the pores or hole can be readily blocked by particulates in the sample gas to be monitored.

To overcome these difficulties, mixed-conducting ceramic membranes have been used as the diffusion barrier for amperometric sensors, as described, for instance, in U.S. Pat. No. 5,543,025 to Garzon, et al. To date, however, the mixed conductors typically have been formed of lanthanum manganese oxide (LSM), lanthanum strontium cobalt oxide (LSC), and terbia-yttria stabilized zirconia (Tb-YSZ). The stability of these mixed conductors is questionable and the reliability of a solid-state gas sensor depends mainly on the stability of the sensing components, particularly the one in contact with exhaust. For example, the stability and reliability of a sensor based on a mixed-conducting membrane depend critically on the stability of the dense mixed-conductor membrane exposed to exhaust containing various pollutants at temperatures up to 1100° C.

It is well known that LSM, LSC, and Tb-YSZ are not very stable in gases containing unburned hydrocarbons and sulfur-containing compounds at high temperatures. These mixed conductors may undergo irreversible structural changes when exposed to unburned hydrocarbons. Further, they may react with sulfur-containing gases at temperatures up to 1100° C., forming reaction products at the surfaces that may alter the electrical properties of the materials. Accordingly, the performance of a sensor based on these mixed conductors may change during the course of operation, leading to drift in sensor output (or lack of stability), and even to sensor failure.

In addition to the chemical stability, the transport properties of the mixed conductors used as the diffusion barrier must not change significantly over the oxygen partial pressure range of interest in order to achieve wide-range oxygen detection. Therefore, the mixed conductors used as the diffusion barrier must have excellent stability under operating conditions to achieve stability, reliability, and reproducibility.

Therefore, there is a need for improved oxygen sensors, systems and methods which address these and other shortcomings of the prior art.

SUMMARY OF THE INVENTION

The present invention is generally directed to an emission control system for determining a concentration of oxygen in a flow of gas using a sensor. In a preferred embodiment, the system includes a sensor which incorporates a diffusion barrier, an electrolyte material, and a counter-electrode. Preferably, the counter-electrode is configured to support the diffusion barrier, and the electrolyte material is disposed between the diffusion barrier and the counter-electrode.

In accordance with another aspect of the present invention, the present invention can also be viewed as providing a method for determining the concentration of oxygen in a flow of gas. In this regard, the method can be broadly summarized by the following steps: providing a sensor in the flow of gas, and providing, from the sensor, a signal corresponding to the concentration of oxygen in the flow of gas. The sensor preferably includes a diffusion barrier, an electrolyte material, and a counter-electrode, with the counter-electrode being configured to support the diffusion barrier, and the electrolyte material being disposed between the diffusion barrier and the counter-electrode.

In accordance with another aspect of the present invention, an alternative method for determining the concentration of oxygen in a flow of gas can be summarized by the following steps: providing a counter-electrode; providing an electrolyte material; depositing the electrolyte material on the counter-electrode; providing a diffusion barrier; depositing the diffusion barrier on the electrolyte material; and co-firing the electrolyte material, the counter-electrode, and the diffusion barrier.

Other features and advantages of the present invention will become apparent to one with skill in the art upon examination of the following drawings and detailed description. It is intended that all such additional features and advantages be included herein within the scope of the present invention.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 7 is a flow chart of a preferred process for producing a preferred embodiment of the emission control system of the present invention.

DETAILED DESCRIPTION OF THE INVENTION

Figure 1:
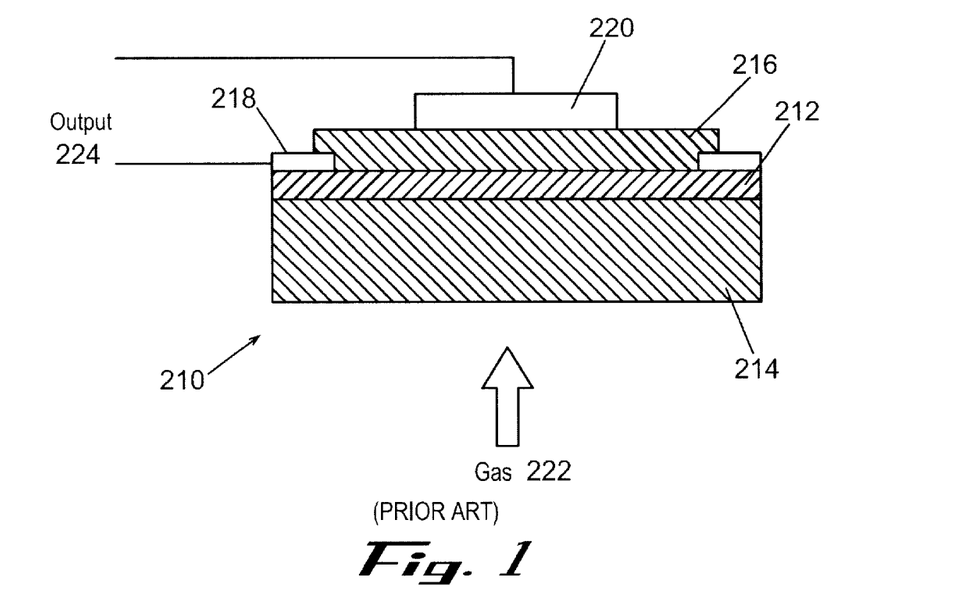
FIG. 1 is a side view of representative prior art sensor.

As described herein before, prior art oxygen sensors typically contain a mixed-conducting ceramic membrane that is used as a diffusion barrier. One example of such a prior art sensor 210 is depicted in FIG. 1. The prior art sensor 210 includes mixed conductor 212 deposited on a porous substrate 214, which may be $Al_2O_3$, and a film of an electrolyte 216 deposited on the mixed layer conductor layer. Electrode pads 218, 220 are suitably deposited on mixed conductor 212 and electrolyte 216, respectively. Gas 222 containing an oxygen content is sampled through porous substrate 214 and a current plateau output 224 is provided. It will be understood that the position of electrolyte 216 and mixed conductor 212 may be reversed, whereby gas 222 is incident directly on mixed conductor 212. Many of the problems and deficiencies of the prior art sensor (mentioned herein before) have been remedied by the present invention.

Figure 2:
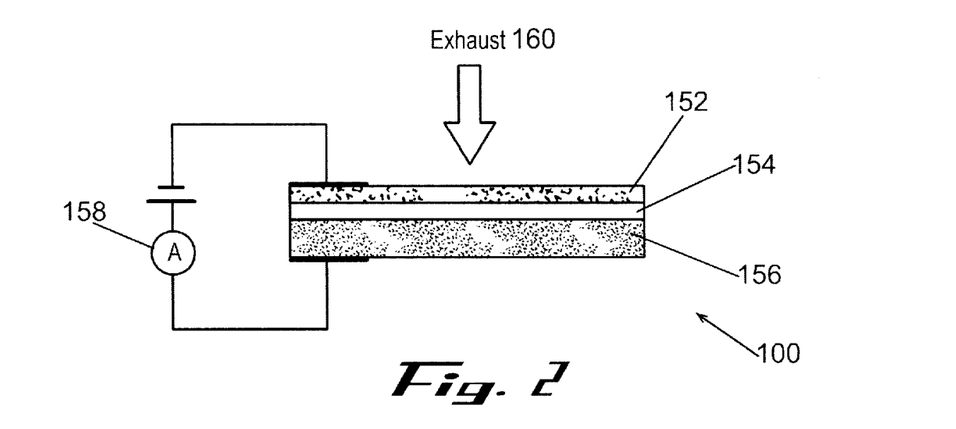
FIG. 2 is a side view of a preferred embodiment of the present invention.

As depicted in FIG. 2, a preferred embodiment of sensor 100 of the present invention incorporates a diffusion barrier 152, and electrolyte material 154, and a counter-electrode 156, with the counter-electrode 156 being configured to support the diffusion barrier 152, and the electrolyte material 154 being disposed between the diffusion barrier 152 and the counter-electrode 156. Preferably, electrodes 155 and 157 are provided which are connected to a monitoring system 158. As depicted in FIG. 2, the sensor 150 may be positioned within a flow of gas, such as exhaust 160, with the exhaust 160 being brought into contact with the diffusion barrier 152, for example.

A preferred embodiment of the present invention uses a dense composite membrane consisting of platinum and yttria-stabilized zirconia (YSZ) as the diffusion barrier 152 for amperometric oxygen sensors because of its high chemical and microstructural stability. To simplify the structure, a preferred embodiment of the present invention uses porous lanthanum strontium manganese oxide (LSM) both as a substrate to support the electrolyte film 154 and as the counter and/or reference electrode for sensor operation and measurements. Because the LSM will be exposed to a reference gas (air), and not to the exhaust 160, the LSM should be adequately stable under the operating conditions. Porous LSM has been used as a cathode for solid oxide fuel cells operated at 1000° C. for more than five years without significant degradation, demonstrating the long-term stability of LSM in air at 1000° C. Thus, in comparison to prior art sensors, the porous supporting substrate, i.e., porous alumina, is eliminated, and the Pt counter electrode is replaced with LSM electrode. The stability and performance characteristics of amperometric oxygen sensors based on a Pt—YSZ composite membrane are discussed hereinafter.

In order to validate successful implementation of the present invention, the following experiments were conducted.

Preparation of Electrolyte Pellets $La_{0.9}Sr_{0.1}Ga_{0.2}Mg_{0.8}O_3$ (LSGM) and YSZ were studied as an electrolyte for the amperometric sensors. LSGM samples were prepared as described in F. Chen and M. Liu, *Transition Metal Oxides Doped LSGM as Electrodes for LSGM Electrolytes*, J. Solid State Electrochem, 3 (1998) 7–14. Stoichiometric amounts of $La_2(CO_3)_3 \cdot xH_2O$, $Ga_2O_3$, $SrCO_3$ and MgO were ball-milled in ethanol for 24 hours and calcined at 1300° C. in air for five hours. X-ray powder diffraction with a Philips PW 1800 was used to examine the phase composition of the calcined product. In case of incomplete calcination, ball-milling and calcination were repeated until pure perovskite phase was obtained. Powders with perovskite phase were crushed using agate mortar and pestle and then ball-milled in ethanol for another twenty-four hours. The resulting fine powder was pressed into pellets of 20 mm diameter and thickness of 2–3 mm. The pellets were sintered at 1450° C. for ten hours to get the dense LSGM pellets. Similarly, powder of yttria-stabilized zirconia, available as TZ-8™ from Tosoh, was pressed to pellets using the same die and sintered at 1350° for five hours. The micro structures of prepared pellets were characterized using a scanning electron microscope (SEM), Model Hitachi S-800. To measure the electrical properties, both surfaces of each sintered LSGM and YSZ pellets were grounded and ultrasonically cleaned before a paste of Pt electrode was screen-printed on them. Pellets with printed Pt electrodes were then fired at 820° C. for ten minutes to form porous Pt electrodes.

Preparation of Fine Platinum Powders and Pt—YSZ Mixed Powder

In a typical experiment, 20 g Pt powder available from Engelhard Corporation was dissolved into 120 ml HCl/$HNO_3$, with a volume ratio of 3:1, to obtain a clear $PtCl_4$ solution with dark orange color, which was then kept at 80 to 90° C. until its volume was reduced to about 80 ml. To this solution, 30 g polyethylene glycol, commercially available as PEG, F.W. 20,000, Alfa Chemical Company, was added under stirring at 80 to 90° C. until a viscous gel was formed, which was then dried using an infrared lamp. The dried gel was ground into powder and fired at 500° C. for two hours to obtain nano-particles of platinum. Alternatively, the prepared $PtCl_4$ solution, yttrium nitrate, commercially available as $Y(No_3)_3 \cdot 6H_2O$, from Johnson Matthey, and zirconium dichloride oxide, commercially available $ZrOCl_2 \cdot 8H_2O$ from Alfa Chem Co. were used as precursors to prepare fine Pt—YSZ composite powders using a sol-gel process. Calculated amount of precursors were dissolved into water and appropriate amount of citric acid and PEG were added to this solution, which was stirred until it became clear. The molar ratio of citric acid to metal ions was 2:1. The PEG was approximately 50% of the weight of the metal and the metal oxide. The solution was then heated up to 80° C. to evaporate solvent and to obtain a gel, which was further dried using an infrared heating bulb. The dried gel was crushed into powders using agate mortar and pestle and followed by calcination at 650° C. for two hours to obtain Pt—YSZ composite powders.

The volume fraction of each phase in the Pt—YSZ composite must be appropriate in order for the layer to function as a mixed-conducting membrane. For a three-dimensional, two-phase composite mixed ionic-electronic conductor (MIEC), like Pt—YSZ, the percolation threshold is found at one-third the volume fraction of the more conductive phase, Pt. The ambipolar conductivity is relatively high when the volume fraction of each phase is in the range of one-third to two-thirds so that both phases are continuous. Accordingly, the volume fraction of Pt in the composite was selected to be 40%. Because the density of platinum is 21.45 g/cm$^3$ and the density of YSZ is 5.89 g/cm$^3$, the weight ratio of Pt to YSZ was chosen to be 2.43.

Preparation of YSZ/Pt—YSZ two Layer Structures Using Uniaxial Pressing

In a typical preparation, 5.000 g YSZ powder, available commercially as TZ-8Y™ from Tosoh, was mixed with 1 g PVA solution, 5 wt% in water, and ground until the binder was dispersed uniformly. In another mortar, 1.000 g Pt, sol-gel powder, was mixed with 0.412 g YSZ and ground in ethanol for 60 min to ensure uniform mixing, followed by the addition of 0.245 g PVA solution, 5 wt% in water, and ground for another ten minutes. First, 0.200 g YSZ-8 was put in die, and then the piston was turned back and forth for three to four times, followed by repress at 0.4 ton for three seconds. Then, 0.100 g Pt—YSZ was spread on the top of the repressed YSZ in die, the piston was turned back and forth for several times to make sure the Pt—YSZ powder is uniform and covers the surface of re-pressed YSZ completely. Finally, the powder was pressed at three tons, holding for 20 seconds to obtain a pressed two-layer pellet, which was then set on YSZ powder and sintered at 1630° C. for five hours.

Electrical Characterization

A computerized impedance analysis system, consisting of a Frequency Response Analyzer, Solartron 1255 and an Electrochemical Interface, Solartron 1286, was used to measure the impedance of the cells in air at temperatures varying from 600 to 800° C. in the frequency range from 65000 Hz to 0.1 Hz. The sensors were tested in a tube furnace and the composition of sample gases was analyzed using an on-line gas chromatography (GC).

RESULTS AND DISCUSSION

Micro structure of Powder and Pellet Electrolytes

An SEM view of the prepared LSGM powder, calcined at 1300° C. in air for five hours, indicated that the average particle size is about 1.4 µm. The surface view of an LSGM pellet sintered at 1450° C. for ten hours indicated that the sintered density was greater than 97% of the theoretical value. An SEM view of the YSZ powder, as received from Tosoh Corporation, showed particle sizes of about 100 nm. The surface view of a dense YSZ pellet, pressed using the Tosoh powder and sintered at 1350° C. for four hours indicated that the average grain size is about 1.5 µm with sintered density close to 100%.

Stability of the Electrolytes

Figure 3:
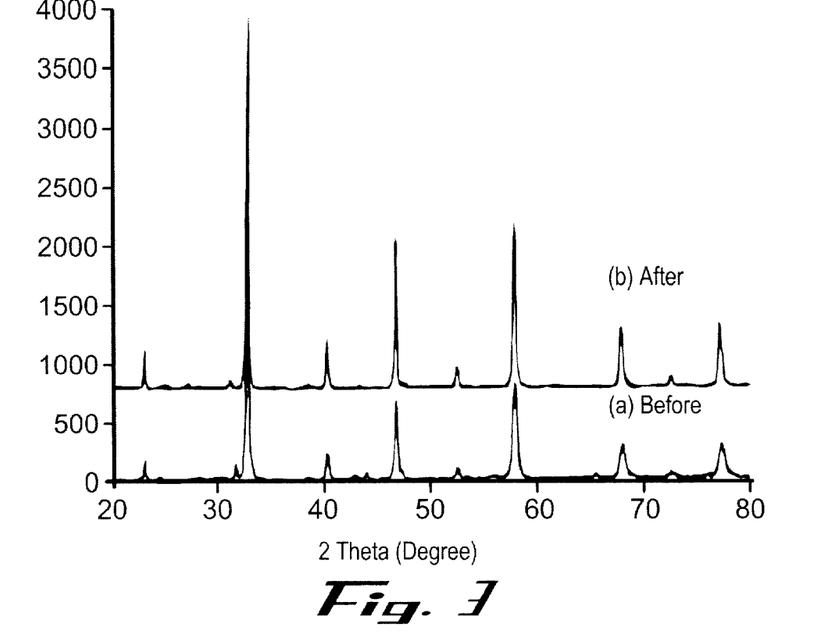
FIG. 3 is a graph of the XRD pattern of an LSGM sample (a) before and (b) after exposure to the exhaust of a gas-fired engine with a thermal history of fifty hours at 820° C., ninety hours at 840° C., and ten hours at 850° C.
Figure 4:
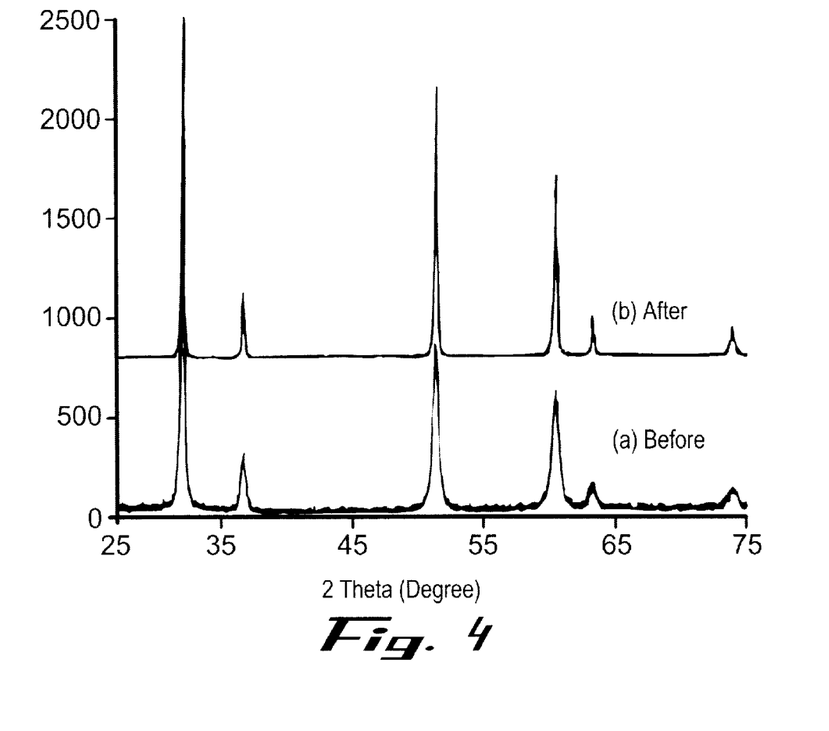
FIG. 4 is a graph of the XRD pattern of YSZ-8 (a) before and (b) after exposure to the exhaust of a gas-fired engine with a thermal history of fifty hours at 820° C., ninety hours at 840° C., and ten hours at 850° C.
Figure 5:
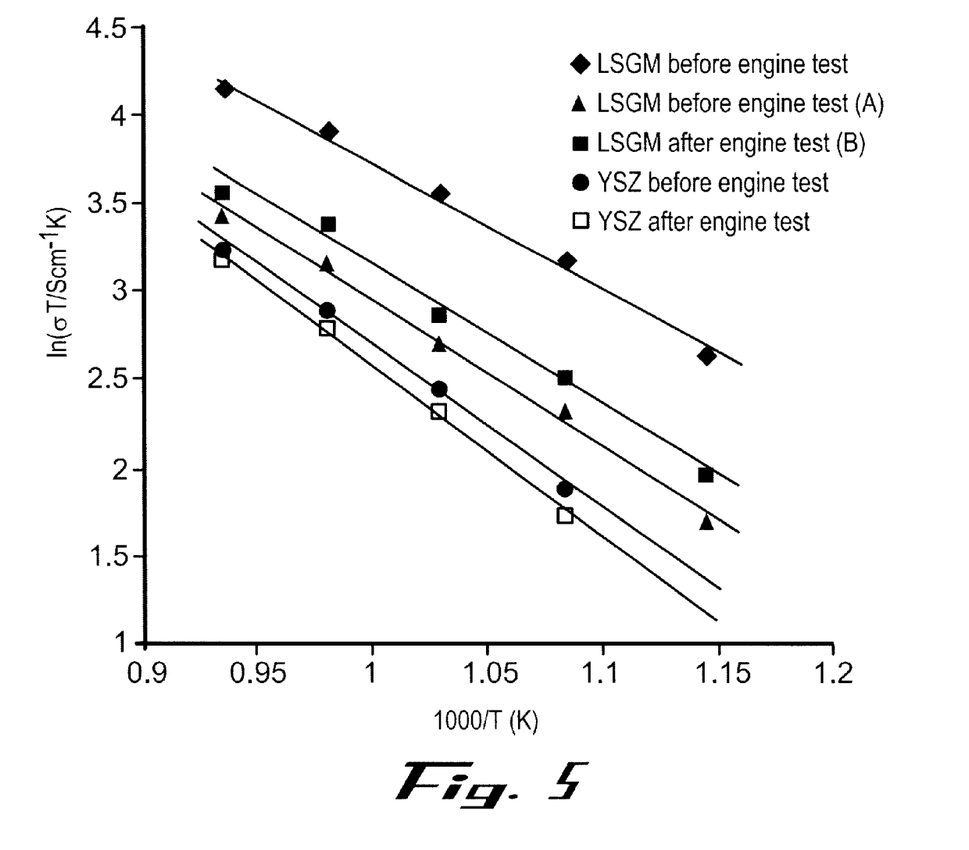
FIG. 5 is a graph representing the conductivities of YSZ-8 and LSGM samples (a) before and (b) after the engine-aging test as calculated from the impedance spectra measured at different temperatures.

To study the stability of the electrolyte materials for the sensor applications, LSGM and YSZ samples were immersed in the exhaust of a gas-fired engine operated at stoichiometric combustion with a thermal history of 50 hours at 820° C., 90 hours at 840° C., and ten hours at 850° C. From the XRD patterns of LSGM and YSZ pellets before and after the aging test, as shown in FIGS. 3 and 4, respectively, it appeared that there were no observable phase changes for both LSGM and YSZ samples. The impedance spectra of LSGM samples before and after the aging test were measured at different temperatures in air and the condictivites of LSGM and YSZ, calculated from the impedance data are summarized in FIG. 5. Clearly, the conductivities of YSZ are within experimental error while the conductivities of LSGM indeed degraded considerably during the aging test, as shown in FIGS. 3 and 4, respectively, implying that the stability of LSGM for the sensor applications may be questionable.

Micro structure of the Composite Layer

The sol-gel derived Pt powder, available from Engelhard Corporation, is very uniform and the average particle size is about 100 nm. The particle size of the Pt powder from Engelhard varies from 0.1 to 0.6 µm. The platinum powders were mixed with Tosoh YSZ powders to form YSZ/Pt—YSZ bi-layer structures. The cross-sectional views of the two samples showed that the Pt—YSZ composite layer using sol-gel derived platinum powder is reasonably dense, whereas that using coarse platinum powder is porous.

In addition, Pt—YSZ composite powders prepared using a sol-gel method were used to press the bi-layer pellets and then sintered in air at 1400° C., 1500° C., and 1600° C. for four hours, respectively. While the surface of each composite layer appears to be dense, the cross-sectional views clearly indicate that they are porous, even for the sample sintered at 1600° C. for four hours. In order to reduce the sintering temperature and increase the sintered density, some other oxides with low melt-point such as $SnO_2$ and $Bi_2O_3$ were used as additives. The results indicated that the addition of $Bi_2O_3$ does not improve the density, and the addition of $SnO_2$ has detrimental effect on the electric properties, although it indeed improved the sintered density.

Sensor Performance

Figure 6:
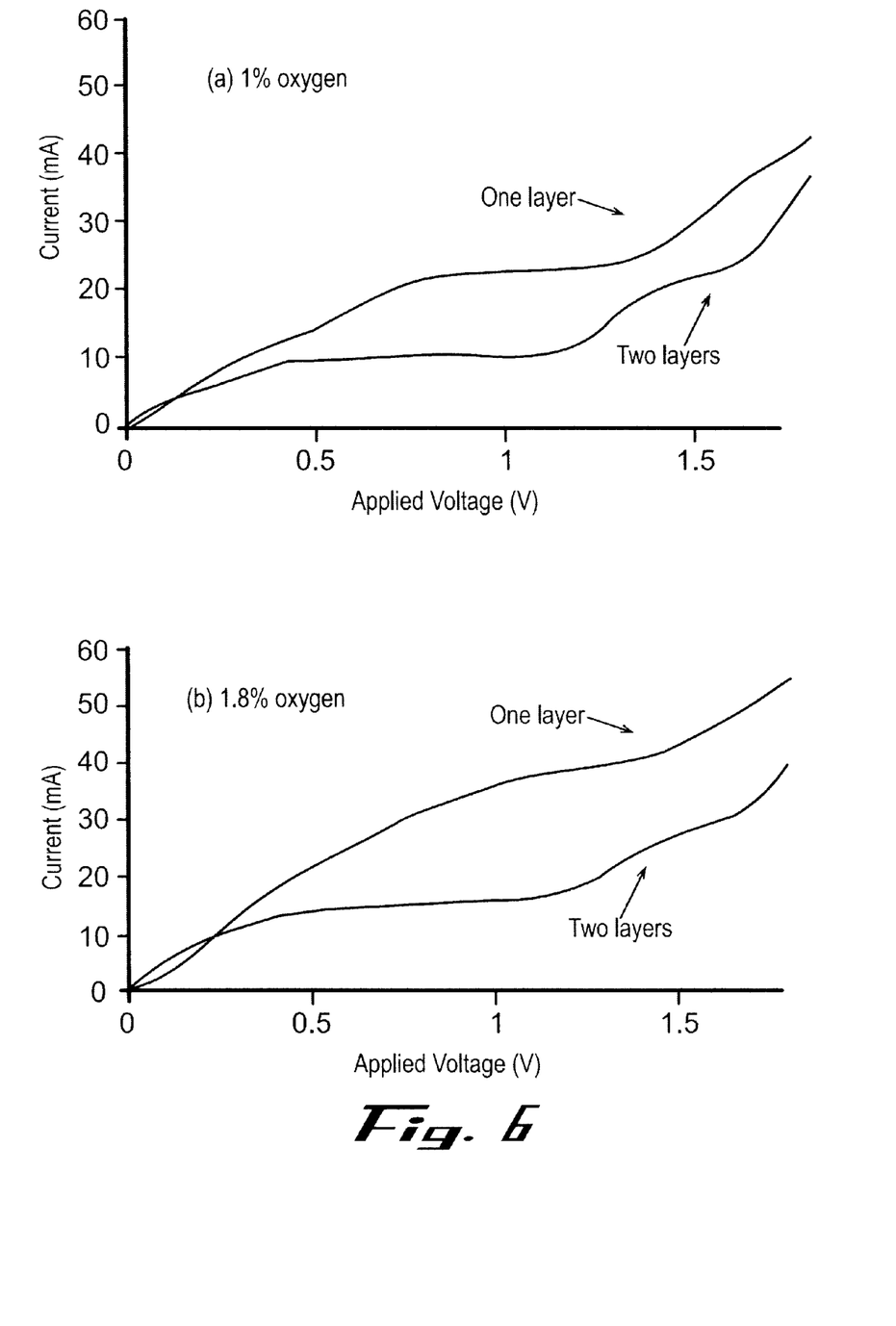
FIG. 6 represents graphs of I–V curves of a sensor (Pt/YSZ/Pt/YSZ) with counter-electrodes of different thicknesses prepared by brush painting, as measured in (a) 0.5% and (b) 1% $O_2$.

In determining sensor performance, some typical I–V curves measured in different oxygen concentrations for a sensor with configuration of Pt/YSZ/Pt—YSZ were viewed. The diffusion-limited currents are flat for oxygen concentrations up to 6%. The diffusion-limited current, measured at 1 Volt, depends linearly on the oxygen concentrations. However, it is not as good as expected for high concentrations of oxygen. Possible causes include inadequate density of the top Pt—YSZ layer; an inefficient counter electrode; and an inappropriate thickness ratio of the YSZ electrolyte to the Pt—YSZ layer. In order to understand the influence of counter electrode on sensor performance, the I–V curves of the sample with one layer counter electrode was measured at 800° under different oxygen concentrations. Then a second layer of Pt was applied to the counter electrode and measured the I–V curves under the same conditions. The results are shown in FIG. 6, indicating that the thickness of the counter electrode has some influence on sensor performance. The electrode should be sufficiently thick so that it will not limit the current passing through the cell.

Further, the thickness ratio of the YSZ to Pt—YSZ was changed from 12:1 to 2:1 and the results show that the thickness ratio of the YSZ electrolyte to Pt—YSZ layer did not have significant effect on sensor performance in the range of thickness ratio studied under the testing conditions.

The flow chart of FIG. 7 shows a preferred method of manufacturing a preferred embodiment of the oxygen sensor present invention. The process begins at block 500 where a counter electrode is provided. The process then proceeds to block 510, where an electrolyte material is provided. Block 520 represents the step of depositing the electrolyte material onto the counter-electrode. In block 530, a diffusion barrier is provided. Block 540 represents the depositing of the diffusion barrier onto the electrolyte material. In block 550, the counter-electrode, electrolyte material, and diffusion barrier are co-fired.

Figure 8:
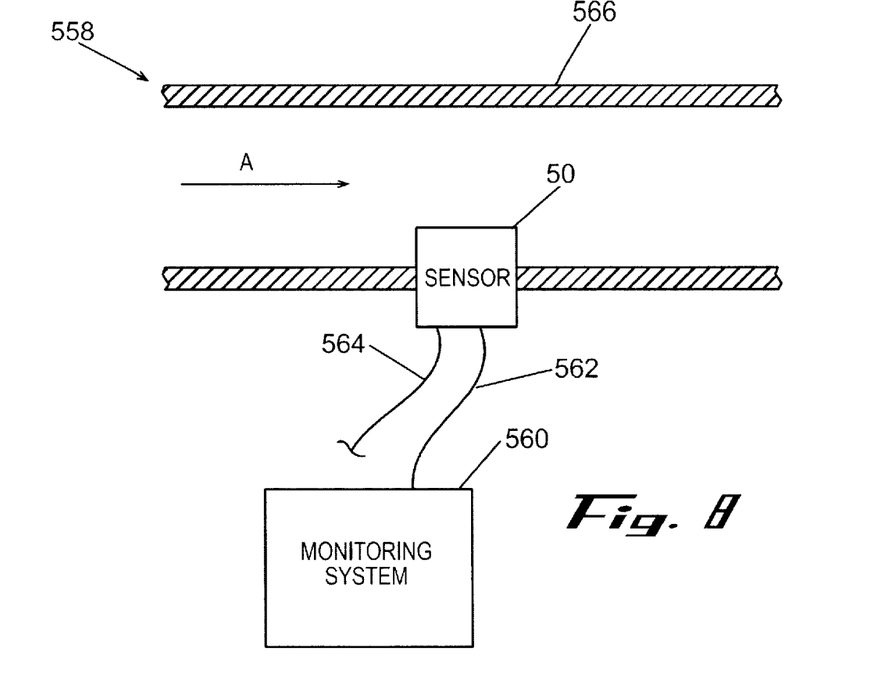
FIG. 8 is a schematic diagram depicting a preferred embodiment of the emission control system.

As depicted in FIG. 8, sensor 150 may be incorporated into an emission control system 558. Preferably, sensor 150 is arranged within a conduit 566 in which a flow of gas is provided, such as in direction A. So configured, at least a portion of the gas contacts a surface of the sensor 150. The monitoring system 560 can be implemented in hardware, software, firmware, or a combination thereof. In some embodiments, the monitoring system may be an analog gauge, for instance. In a preferred embodiment, however, the monitoring system preferably is configured as a special purpose computing apparatus for implementing logical functions. A monitoring system 560 is attached to the sensor 150, preferably, by means of platinum wires 562.

The monitoring system can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions. In the context of this document, a "computer-readable medium" can be any means that can contain, store, communicate, propagate or transport the program for use by or in connection with the instruction execution system, apparatus, or device. The computer readable medium can be, for example, but not limited to, an electronic, magnetic, optical, electro-magnetic, infrared, or semi-conductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (magnetic), a read-only memory (ROM) (magnetic), an erasable, programmable, read-only memory (EPROM or Flash memory) (magnetic), an optical fiber (optical), and a portable compact disk read-only memory (CDROM) (optical). Note that the computer-readable medium could even be paper or another suitable medium upon which the program is printed, as the program can be electronically captured, via for instance, optical scanning of the paper or other medium, then compiled, interpreted, or otherwise processed in a suitable manner, if necessary, and then stored in a computer memory.

Figure 9:
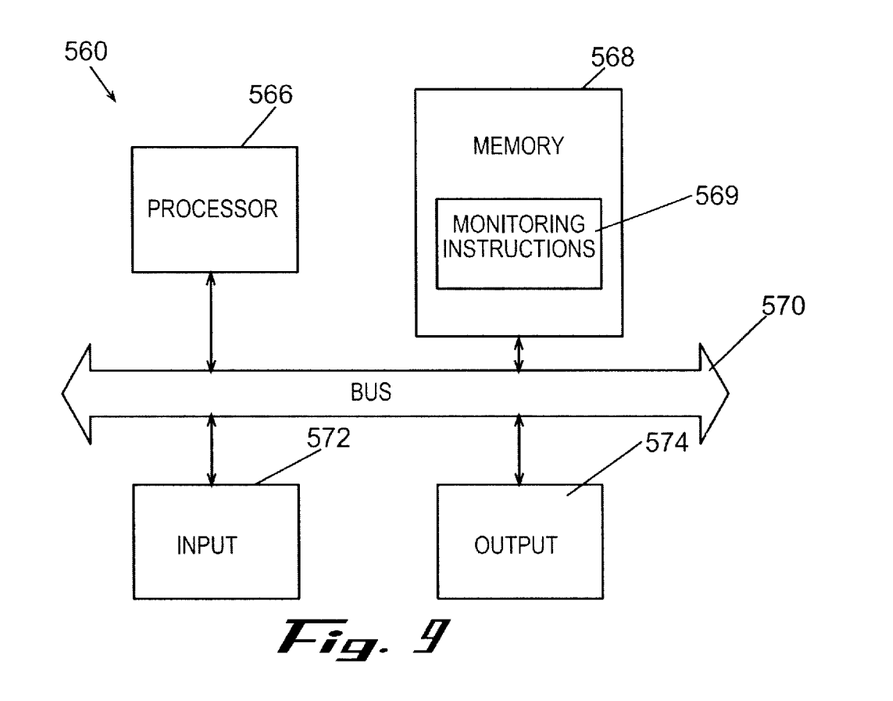
FIG. 9 is a schematic diagram of the monitoring system depicted in FIG. 9.

FIG. 9 illustrates a preferred embodiment of the monitoring system 560, i.e., a processor-based system, which may be utilized by the present invention. As shown in FIG. 9, the monitoring system 560 generally comprises a processor 566, a memory 568. Herein, the memory 568 may be any combination of volatile and nonvolatile memory elements, such as random access memory or read-only memory. The monitoring system 560 monitors the amount of oxygen detected by the sensor. The processor 566 accepts monitoring 569 instructions and other data from memory 568 over a local interface 570, such as a bus(es). The monitoring system 560 also includes an input 572, such as wire 562 (FIG. 8), and an output 574, such as a display, for instance.

Experimental

Preparation of LSM Using a Sol-gel Process

Figure 10:
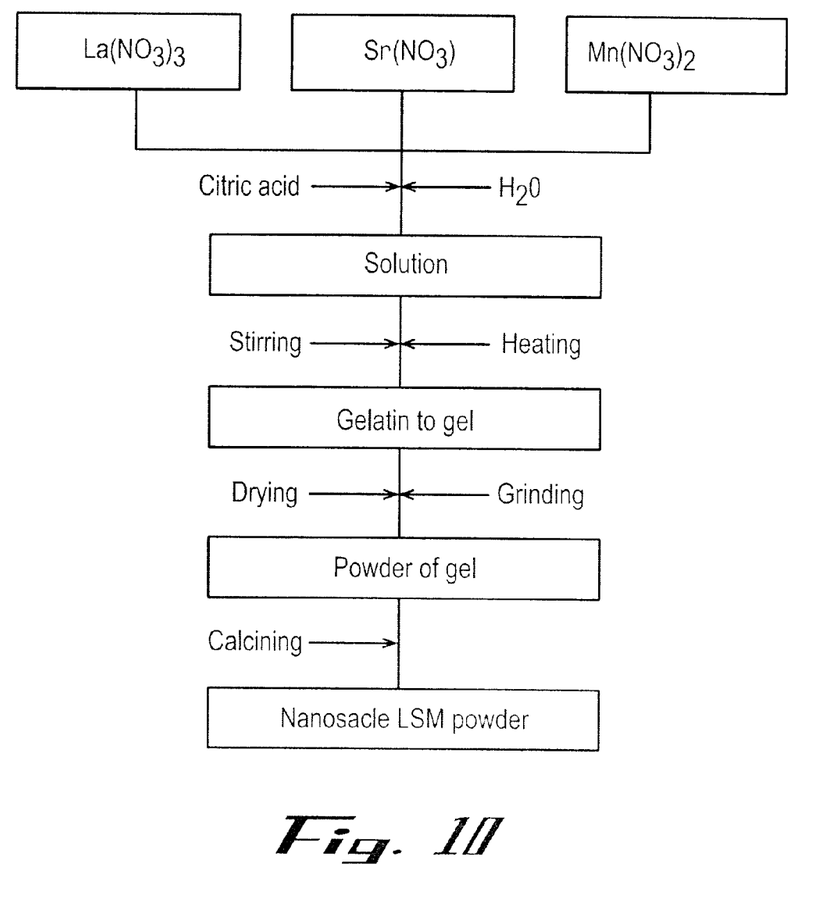
FIG. 10 is a flow chart depicting a preferred method for preparing fine LSM powders.

Schematically shown in FIG. 10 is a flow chart for the preparation of fine LSM powders. Stoichiometric amount of $La(NO_3)_3$, $6H_2O$ (99.99%), $Sr(NO_3)_2$, and $Mn(CH_3COO)_2 \cdot 4H_2O$) were dissolved in water, to which citric acid was added under stirring. The molar ration of metal ions to critic acid was 1:2. Once a clear solution was obtained, it was heated up to 85–90° C. under continuous stirring to evaporate the solvent until gelation occurred. The gel was further dried using an infrared heater and then ground to powders, which was subsequently fired at different temperatures in air for different periods of time to get powders of different particle sizes. In order to increase the porosity of the LSM substrate, 10% (weight) rice starch was added to LSM powder, followed by ball-milling in ethanol for twenty-four hours. After drying at 80° C. under stirring, the powder was pressed into pellets using uniaxial pressing, about 0.8–1 g for each pellet. These pellets were used as the substrates for the deposition of the YSZ and Pt—YSZ films.

Preparation of YSZ Films Using an EPD Method.

Suspensions of YSZ powder were prepared by dispersing YSZ powder (Tosoh TZ-8Y) and dissolving iodine in acetone. The reaction between acetone and iodine, $$CH_3COCH_3 + I_2 \rightleftharpoons ICH_2COCH_2I + 2H^+ \tag{1}$$

produces protons which are absorbed on the YSZ particles, leading to positively charged YSZ particles. In fact, the zeta potential of YSZ particles in pure acetone is almost zero, but increases with concentration of $I_2$. Under the influence of an applied electric field, the ionic current passing through the suspension is carried not only by the charged oxide particles but also by free ions coexisting in the suspension. However, the amount of free ions is generally small in organic suspension, such as acetone so that the contribution of the free ions may be ignored. The weight (g) of charged particles deposited per unit area of electrode can be approximated by:

$$w = 2/3 C \epsilon_o \epsilon_r \zeta \eta^{-1} E L^{-1} t \tag{2}$$

where C represents the concentration of the particles (g/L), $\epsilon_o$ the permittivity of vacuum, $\epsilon_r$ the relative permittivity of the solvent, $\zeta$ the zeta potential of the particle, $\eta$ the viscosity of the suspension, E the applied potential, L the distance between electrodes, and t the deposition time. Thus, the weight of deposited oxide particles, and hence the thickness of the oxide film, can be readily controlled through various deposition parameters.

Figure 11:
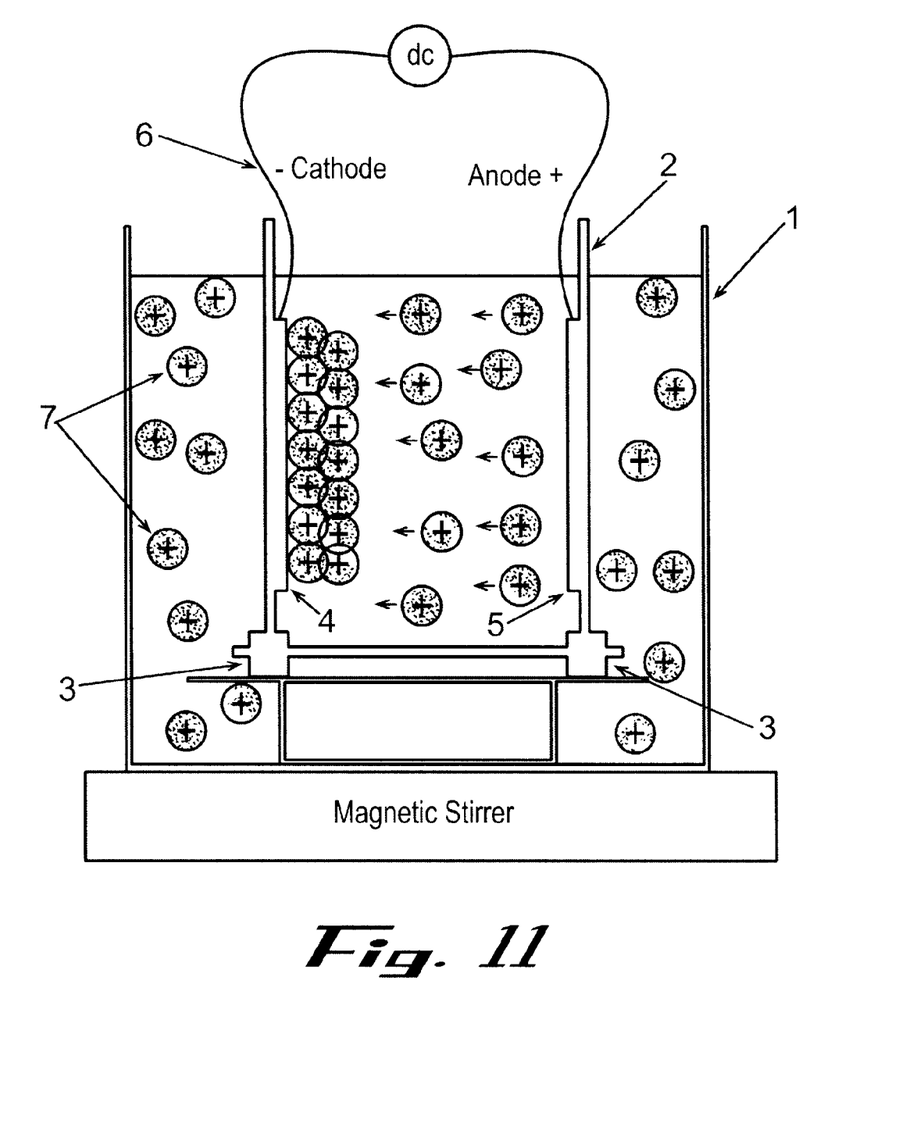
FIG. 11 is a cut-away side view of the experimental apparatus for the preparation of the YSZ thin film using an EPD process, with beaker 1, teflon holder 2, screws 3, substrate (LSM pellet) 4, metal electrode (Pt disc) 5, wire 6, and charged YSZ particles 7.

Schematically shown in FIG. 11 is the apparatus used for deposition of YSZ film on LSM substrate using EPD. LSM substrate was used as negative electrode, and a platinum disc was used as the positive electrode. The concentration of $I_2$ and the concentration of YSZ powder in this suspension was kept at 0.5 g/L and 10 g/L, respectively. The applied voltage between the two electrodes was varied from 10 to 30 V and the deposition time was varied from 5 to 30 minutes. The suspension was continuously stirred using a magnetic spin bar to maintain the uniformity of the solution during deposition.

Preparation of Composite Film of Platinum and YSZ (Pt—YSZ)

a. Colloidal Deposition.

Platinum ink (Engelhard) and Tosoh powder, of average particle size of about 0.1 µm, were used to prepare colloidal solution of Pt—YSZ composite. A mixture of them was dispersed for 30 minutes in alcohol, weight ratio of solid to liquid was 1:5, using an ultrasonic processor, GE 130, VWR, to obtain a colloidal solution. The colloidal solution was then deposited on the top of a green YSZ film, prepared using EPD, using a drop coating or a spin coating process, followed by drying at 90° C. for twelve hours and 120° C. for twelve hours.

b. Sol-gel Process.

An amperometric oxygen sensor using a dense Pt—YSZ composite layer as a diffusion barrier offers very high chemical and micro structural stability. To date, however, the sensors of this type were fabricated by uniaxial pressing. There are a few practical problems with this fabrication method. First, the typical thickness of the Pt—YSZ layer is about 100–500 µm, making the sensor expensive, due to the amount of platinum used. Second, the pressed compacts must be sintered at 1630° C. in order to achieve the required density. More importantly, the YSZ electrolyte is too thick, 500 µm, and it is functional only at high temperatures. The sol-gel process provides a solution to these problems.

Ten mg Pt powder, available from Engelhard, was dissolved into a mixture of 20 ml nitrate acid and 60 ml hydrochloric acid to form $PtCl_4$ solution, which was kept at 80° C. until its volume reduced to about 50 ml. The color changed to dark. The concentration of Pt ions in the $PtCl_4$ solution is about 0.2 g/ml. Then, calculated amounts of $ZrOCl_2 \cdot 8H_2O$ and $Y(NO_3)_3 \cdot 4H_2O$ were dissolved in an appropriate amount of $PtCl_4$ solution. The weight ratio of Pt to YSZ was kept at about 3.5 to obtain a Pt—YSZ composite with 40% (Volume) of Pt. The obtained solution was kept at 80° C. under stirring until its volume reduced to half, in order to increase its concentration. Then, a polymer surfactant such as polyethylene oxide (PEO) or polyethylene glycol (PEG) was added to the solution to increase the viscosity of the solution and to maintain the uniformity of the gel films during drying. The amount of the polymer was about 10 wt % of the Pt and YSZ. The final solution was used to fill the pores in green Pt—YSZ composite films using a spin-coating process.

c. Preparation of Polymer Films.

Since the green Pt—YSZ and YSZ films are porous, the solution of Pt—YSZ may go through the YSZ film and filtrate into LSM substrate during the filling process, leading to shortage between Pt—YSZ and LSM. In order to prevent this, an intermediate organic film without metal ions was prepared on the surface of the porous green YSZ films before deposition of Pt—YSZ colloidal or sol solution. A suitable organic film for this purpose should have good wettability to the porous green films and to the Pt—YSZ sol solution. The organic film used in this study was produced as follows. First, citric acid was dissolved in ethylene glycol, with a molar ration of ethylene glycol to citric acid of 3. The resultant mixture was then heated to 80° C. to promote polyesterification and resin formation. When the mixture became viscous, the solution was ready for coating.

After the organic film was prepared on the surface of green YSZ film, the sample was subjected to drying at 100° C. for three hours and the Pt—YSZ colloidal and sol film were then deposited using a spin-coating method. This sample was dried at 80° C. for three hours, followed by firing at 500° C. for thirty minutes with a heating rate of 1° C./min from room temperature to 500° C., to remove the organics. The Pt—YSZ solution filling and subsequent firing at 500° C. were repeated for a few more times as needed to increase the density of Pt—YSZ film. Finally, the sample was co-fired at 1250° C. to obtain the dense Pt—YSZ/YSZ films on the porous LSM substrate. Although other polymers such as PEG and PVA were also used, they always caused cracking during drying at high temperatures, probably due to excessive shrinkage of the polymers.

RESULTS AND DISCUSSION

Characteristics of LSM Powders and Porous LSM Substrates

Figure 12:
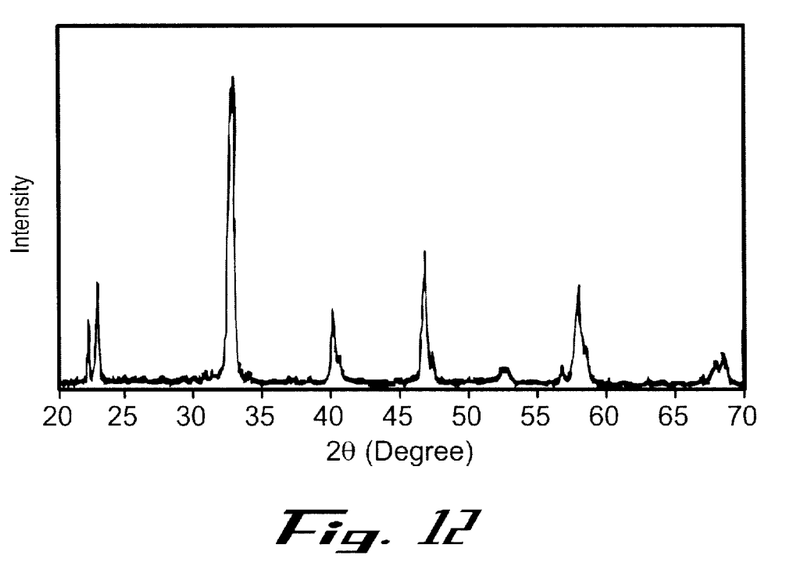
FIG. 12 is a graph of the X-ray diffraction pattern of the LSM powder, fired at 550° C. in air for three hours.

Shown in FIG. 12 is an X-ray diffraction (XRD) pattern of the LSM powder derived from a sol-gel process, implying that the LSM powder, fired at 550° C. for two hours, has a perovskite structure. This temperature is much lower than calcination temperature needed to form perovskite LSM, which is about 800 to 1000° C., when a traditional ceramic process is used. A transmission electron microscope (TEM) micrograph of the sol-gel derived LSM powder indicated that the average particle size is about 40 nm.

The micro structure of LSM substrates sintered at 1150° C. and 1250° C. for three hours, respectively, showed that while the grain size of LSM increased dramatically during sintering, the final porosity of the substrate is about 36%, adequate for electrode applications. Another very important point is the large shrinkage of the LSM substrate using powders derived from the sol-gel method. Due to the small particle size and large amount of pore former, rice starch in the form of green pellets, the shrinkage of LSM substrates is about 23%, much larger than those prepared using a traditional ceramic process, which is about 17%. It is believed that this large shrinkage plays an important role in assisting densification of the YSZ and Pt—YSZ film during sintering.

Micro structure of YSZ Film

The surface of the YSZ film produced by the instant process is smooth and uniform. Preparation of high quality green YSZ film is the most important step for the preparation of dense YSZ film on porous substrate. The quality of green film is influenced by many process parameters. In particular, the concentration of the suspension, the applied voltage, and the deposition time are the most important parameters. If the concentration of YSZ in the suspension is too high, the deposition rate of YSZ particles would be very fast, leading to poor packing density of the green YSZ film with pores or pinholes. The same is true when the applied voltage is too high. At a given concentration of YSZ in the suspension and an applied voltage between the two electrodes, the thickness of the green YSZ film is primarily determined by the deposition time. Typically, it is difficult to obtain a crack-free green film when the film is too thick.

Acetone has small surface tension but high evaporation rate; it dries too fast when the film was taken out from the solvent, leading to cracks in the green YSZ films. Ethanol has slower evaporating rate, but its surface tension is larger than acetone, which leads to the sliding down of the YSZ film deposited on the surface of the porous substrate when the film was taken out from the suspension. In order to overcome these problems, a mixture of 75% V acetone and 25% V ethanol was used in the present experiment.

The conductivity of LSM substrate is also an important parameter for the deposition of green YSZ film. Low conductivity of substrate will lead to non-uniform green film and slow deposition.

The micro structures of YSZ films on LSM substrates fired at different temperatures showed that while the film fired at 1150° C. for three hours is still porous, the film fired at 1250° C. for three hours is very dense. The thickness of the dense film is about 7.5 $\mu$m.

These results clearly demonstrated that dense YSZ thin films can be prepared on porous LSM substrate of sol-gel derived powder at temperatures as low as 1250° C., which is about 200° C. lower than other film deposition approaches reported in the literature.

Microstructure of Pt—YSZ Composite Film

Several processes have been studied for the preparation of Pt—YSZ composite film. From an SEM micrograph, it can be seen that the YSZ layer is dense, the LSM substrate is porous, but the Pt—YSZ composite layer is not as dense as required for an amperometric sensor using the Pt—YSZ as diffusion barrier. However, the structure is desirable for solid oxide fuel cells or other electrochemical functions where both electrodes must be porous.

Several factors may influence the density of the top Pt—YSZ layer. One possibility is that the platinum particle size is too large. As discussed elsewhere, the composite consisting of coarse platinum powder and Tosoh YSZ is still porous after being sintered at 1630° C. for five hours while sol-gel derived platinum and Tosoh YSZ is completely dense under the same conditions. Thus, a combination of the colloidal and the Pechini process was sued to prepare dense Pt—YSZ composite films.

First, the surface of the YSZ film was coated with a blank polymer film as described earlier to prevent infiltration of Pt solution into the green YSZ film. Second, a colloidal solution of Pt—YSZ was deposited on the top of the polymer-coated YSZ film to obtain a Pt—YSZ film. Third, a Pechini process was used to fill the pores in the colloidal film of Pt—YSZ using a Pt—YSZ solution. Finally, all layers on an LSM substrate were cofired at 1250° C. for three hours to obtain dense YSZ and Pt—YSZ films on a porous LSM substrate.

It is clear from an SEM micrograph that the surface of the Pt—YSZ film is completely dense and pin-hole free. The cross-sectional views show that both YSZ and Pt—YSZ films are reasonably dense while the LSM substrate is still porous, a desired structure for an amperometric sensor. It is believed that the small particles from the Pt—YSZ solution not only reduce the porosity of Pt—YSZ colloidal film, but also improve the sintering behavior of the composite film. The small particles sitting among big colloidal particles may act as the bridge between large particles for mass transport and densification during sintering, resulting in reduced sintering temperature and increased density of Pt—YSZ composite films.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. An emission control system for determining a concentration of oxygen in a flow of gas comprising:
   a sensor having
      a diffusion barrier, wherein the diffusion barrier also serves as a sensing electrode and comprises a dense composite membrane consisting of yttria-stabilized zirconia and a noble metal;
      an electrolyte material, and a
      counter electrode, the counter electrode being configured to support the diffusion barrier, and the electrolyte material being disposed between the diffusion barrier and the counter electrode.

2. The emission control system of claim 1, further comprising a conduit configured to deliver the flow of gas to the sensor.

3. The emission control system of claim 1, further comprising a conduit configured to deliver the flow of gas to the diffusion barrier.

4. The emission control system of claim 1, wherein the diffusion barrier is oriented to receive the flow of gas such that the counter electrode is downstream of the diffusion barrier.

5. The emission control system of claim 1, wherein the noble metal is platinum.

6. The emission control system of claim 1, wherein the electrolyte material is selected from the group consisting of: yttria-stablized zirconia, ceria, and bismuth oxide.

7. The emission control system of claim 1, wherein the counter electrode is a mixed oxide.

8. The emission control system of claim 7, wherein the mixed oxide is lanthanum strontium manganese oxide.

9. The emission control system of claim 7, wherein the mixed oxide is porous.

10. The emission control system of claim 1, wherein the counter electrode is porous.

11. The emission control system of claim 1, wherein the emission control system is tubular.

* * * * *

UNITED STATES PATENT AND TRADEMARK OFFICE
CERTIFICATE OF CORRECTION

PATENT NO.    : 6,440,283 B1
DATED         : August 27, 2002
INVENTOR(S)   : Liu It is certified that error appears in the above-identified patent and that said Letters Patent is hereby corrected as shown below:

Column 4,
Line 65, delete "Y(No$_3$)$_3$.6H$_2$O" and replace with -- Y(NO$_3$)$_3$•6H$_2$O --.
Line 66, delete "ZrOCl$_2$.8H$_2$O" and replace with -- ZrOCl$_2$•8H$_2$O --.

Column 6,
Line 19, delete "condictivites" and replace with -- conductivities --.

Column 8,
Line 19, delete "ration" and replace with -- ratio --.
Line 19, delete "critic" and replace with -- citric --.

Column 9,
Line 64, delete "ration" and replace with -- ratio --.

Column 11,
Line 37, delete "sued" and replace with -- pursued --.

Signed and Sealed this

Eleventh Day of February, 2003

JAMES E. ROGAN
*Director of the United States Patent and Trademark Office*